(12) United States Patent
Gil et al.

(10) Patent No.: US 7,887,546 B2
(45) Date of Patent: Feb. 15, 2011

(54) SURGICAL INSTRUMENT AND METHOD OF USE FOR FACILITATING POSITIONING OF AN OSTEOCHONDRAL PLUG

(75) Inventors: Carols E. Gil, Collierville, TN (US); Jeetendra S. Bharadwaj, Memphis, TN (US); Michael A. Dupree, Munford, TN (US)

(73) Assignee: Warsaw Orthopedic, Inc.

( * ) Notice: Subject to any disclaimer, the term of this patent is extended or adjusted under 35 U.S.C. 154(b) by 0 days.

(21) Appl. No.: 12/794,395

(22) Filed: Jun. 4, 2010

(65) Prior Publication Data

US 2010/0249858 A1 Sep. 30, 2010

Related U.S. Application Data

(62) Division of application No. 11/554,936, filed on Oct. 31, 2006, now Pat. No. 7,758,583.

(51) Int. Cl.
| | |
|---|---|
| *A61B 17/56* | (2006.01) |
| *A61B 17/58* | (2006.01) |
| *A61B 17/88* | (2006.01) |
| *A61F 2/02* | (2006.01) |
| *A61F 2/28* | (2006.01) |

(52) U.S. Cl. .................. 606/99; 606/86 R; 606/88; 606/95; 606/110; 606/113; 606/182

(58) Field of Classification Search .............. 606/86 R, 606/88–89, 95, 99, 110, 113, 182
See application file for complete search history.

(56) References Cited

U.S. PATENT DOCUMENTS

| | | | |
|---|---|---|---|
| 5,197,967 | A | 3/1993 | Wilson |
| 5,722,977 | A | 3/1998 | Wilhelmy |
| 5,772,664 | A | 6/1998 | DeSatnick et al. |
| 5,833,628 | A | 11/1998 | Yuan et al. |
| 6,017,348 | A | 1/2000 | Hart et al. |
| 6,598,588 | B2 | 7/2003 | Yuya |
| 6,767,354 | B2 | 7/2004 | Johanson et al. |
| 6,852,114 | B2 | 2/2005 | Cerundolo |
| 2004/0210246 | A1 | 10/2004 | Johanson et al. |

OTHER PUBLICATIONS

Gil et al., "Osteochondral Repair Assembly Including Retracting SPacer, Kit and Method," U.S. Appl. No. 11/390,320, filed Mar. 28, 2006.

*Primary Examiner*—Thomas C Barrett
*Assistant Examiner*—Sameh Boles

(57) ABSTRACT

A surgical instrument and method are provided for positioning an osteochondral plug within a bone defect site. The instrument includes an elongate shaft, a ribbon, an elongate sleeve and a locking mechanism. The shaft has proximal and distal ends, with the distal end being shaped to contact the osteochondral plug. The ribbon extends along two sides of the shaft and around the distal end, forming a loop that is used to secure the osteochondral plug to the distal end. The sleeve is movably mounted to the shaft for reciprocating relative thereto between retracted and extended positions. The sleeve includes a slot that allows for visualization and cutting of the ribbon. The locking mechanism locks the ribbon in place and thereby controls the size and tension of the loop that surrounds the osteochondral plug, securing it to the distal end of the shaft.

6 Claims, 6 Drawing Sheets

SURGICAL INSTRUMENT AND METHOD OF USE FOR FACILITATING POSITIONING OF AN OSTEOCHONDRAL PLUG

CROSS-REFERENCE TO RELATED APPLICATIONS/PATENTS

This application is a divisional of U.S. application Ser. No. 11/554,936, filed Oct. 31, 2006, which is hereby incorporated by reference in its entirety. This application also contains subject matter which is related to the subject matter of the following application, which is hereby incorporated herein by reference in its entirety:

"Osteochondral Repair Assembly Including Retracting Spacer, Kit and Method," by Gil et al., U.S. Ser. No. 11/390,320, filed Mar. 28, 2006.

TECHNICAL FIELD

The present invention relates generally to the field of surgery and osteochondral grafting, and more particularly, to surgical instruments and methods for positioning an osteochondral bone plug within a defect site of a patient.

BACKGROUND OF THE INVENTION

Human joint surfaces are covered by articular cartilage that provides a resilient, durable surface with low friction. Cartilage is an avascular tissue that has a small number of chondrocytes encapsulated within an extensive extracellular matrix. The cartilage acts to distribute mechanical forces and to protect subchondral bone. The knee is a particular instance of a cartilage surfaced (the condyle) bone area. The knee comprises three bones—the femur, tibia, and patella that are held in place by various ligaments. Corresponding chondral areas of the femur and the tibia form a hinge joint and the patella acts to protect the joint. Portions of the chondral areas as well as the undersurface of the patella are covered with articular cartilage that allows the femur, patella and tibia to smoothly glide against each other without causing damage.

Damage to the articular cartilage, subchondral bone or both can result from traumatic injury or a disease state. For example, articular cartilage in the knee can be damaged due to traumatic injury as with athletes and via a degenerative process as with older patients. The knee cartilage does not heal well due to the lack of vascularity. Hyaline cartilage in particular has a limited capacity for repair and lesions in this material, without intervention, can form scar tissue lacking the biomechanical properties of normal cartilage.

A number of procedures are used to treat damaged articular cartilage. Currently, the most widely used procedure involves lavage, arthroscopic debridement and repair stimulation. Repair stimulation is conducted by several methods including, drilling, abrasion arthroplasty and microfracture. The goal of these procedures is to penetrate into subchondral bone to induce bleeding and fibrin clot formation. This reaction promotes initial repair. However, the resulting formed tissue is often fibrous in nature and lacks the durability of normal articular cartilage.

Another known treatment involves the removal and replacement of the damaged articular cartilage with a prosthetic device. However, historically, artificial prostheses have largely had limited success since they are non-elastic, and therefore lack the shock-absorbing, properties characteristic of the normal cartilage. Moreover, the known artificial devices have shown a reduced ability to withstand the high and complex forces inherent to routine knee joint function.

In an attempt to overcome the problems associated with the above techniques, osteochondral transplantation, also known as "mosaicplasty" or "OATS" has been used to repair articular cartilage. This procedure involves removing injured tissue from the articular defect and drilling cylindrical openings in the area of the defect and underlying bone. Cylindrical plugs, consisting of healthy cartilage overlying subchondral bone, are harvested from another area of the patient, typically from a lower weight-bearing region of the joint under repair, or from a donor patient, and are implanted in the host openings. However, in these cases, if the opening is too large, the graft can rotate or move within the host site and become loose, which will prevent bio-integration with the surrounding tissues. Further, if the host site is too small, significant tissue and cellular damage can occur to the graft during the implantation.

Historically, osteochondral grafting has been used successfully to repair chondral damage and to replace damaged articular cartilage and subchondral bone. First, in this procedure, cartilage and bone tissue of a defect site are removed by routing to create a cylindrical bore of a precise geometry. Then a cartilage and subchondral bone plug graft is harvested in a matching geometry. The donor plug graft is typically removed from another body region of less strain. The donor plug graft can be harvested from a recipient source (autograft) or from another suitable human or other animal donor (allograft). The harvested plug graft is then implanted into the bore of the routed defect site. Healing of the plug graft to the host bone results in fixation of the plug graft to the surrounding host region.

Success of the grafting process is dependant on the intimate seating of the graft within the socket. First, surface characteristics of the plug graft are critical. For the procedure to be successful, the surface of the transplanted plug graft must have the same contour as the excised osteochondral tissue. If the contour is not a correct match, a repaired articular surface is at risk for further damage during motion. Additionally, some graft shapes do not pack well into irregular defects. The graft may have a propensity to rotate resulting in poor integration of the graft to the surrounding host tissue. An improperly placed plug graft can result in host tissue integration failure and post implantation motion.

Since the plug graft is press-fit within a recipient socket, removal or repositioning can cause irreparable damage that can render a graft useless. Hence, a surgeon has only one opportunity to properly press fit the graft into the host site. If the graft is placed too shallow or too deep or otherwise incorrectly, the graft cannot be removed for proper positioning by typical procedures or tools. Extraction procedures and tools can cause further damage to the boundary host site cells and to the graft structural integrity.

Thus, there is a need for a surgical instrument to which a donor plug may be secured and method of use to permit flexible donor graft plug placement and replacement, if necessary without causing damage to the host site or the donor plug.

SUMMARY OF THE INVENTION

The present invention comprises a surgical instrument and methods for securing a graft plug to an instrument, facilitating positioning of a graft plug within a bone defect and fabricating an instrument to be used when implanting a bone graft plug within the body. The instrument and methods disclosed herein employ an instrument-to-plug graft attachment approach that is of sufficient strength for the surgical instrument to be readily utilized to accurately position and implant the bone plug graft. Further, the securement approach provides for detachment and removal of the surgical instrument while the bone plug graft remains within the body.

More particularly, the present invention provides in one aspect, a surgical instrument for positioning an osteochondral plug within a bone defect site. The surgical instrument includes an elongate shaft having proximal and distal ends which define a longitudinal axis extending therebetween. The distal end of the elongate shaft is configured and shaped to allow intimate contact with the osteochondral plug. Further, a ribbon extends along the sides of the elongate shaft and forms a loop at the distal end of the elongate shaft. When in use, the loop is appropriately sized to secure the osteochondral plug to the distal end of the elongate shaft.

The present invention provides in another aspect, a surgical instrument that includes an elongate shaft having proximal and distal ends that define a longitudinal axis extending therebetween. The distal end of the elongate shaft is configured to contact the osteochondral plug. The surgical instrument also includes a ribbon that extends along the sides of the elongate shaft and forms a loop at the distal end of the elongate shaft. During use of the surgical instrument, the loop is sized to hold and secure the osteochondral plug to the distal end of the elongate shaft. Further, the surgical instrument has an elongate sleeve that includes proximal and distal ends with a longitudinal axis extending therebetween. The elongate sleeve surrounds the elongate shaft, facilitating the holding of the ribbon in place relative to the elongate shaft. In addition, the surgical instrument includes a locking mechanism that is positioned near the proximal end of the elongate shaft and functions to secure the ribbon to the elongate shaft when the locking mechanism has be placed in a locked position.

Another aspect of the present invention provides a method for grasping an osteochondral plug. The method includes the step of employing a surgical instrument having an elongate shaft with proximal and distal ends that define a longitudinal axis extending therebetween. The distal end of the elongate shaft is configured to contact the osteochondral plug. Also included in the surgical instrument is a ribbon extending along the elongate shaft that forms a loop at the distal end of the elongate shaft that is sized to receive the osteochondral plug. Further included in the surgical instrument is a locking mechanism that is located near the proximal, end of the elongate shaft. The method includes the steps of placing the osteochondral plug within the loop of the ribbon and then pulling or providing tension to the one of the ends of the ribbon so to adjust the length of the ribbon and size of the loop, causing the loop to tighten around the osteochondral plug. The method includes the further step of engaging the locking mechanism to secure the ribbon relative to the elongate shaft, resulting in the fixation of the osteochondral plug to the distal end of the elongate shaft.

The present invention provides in yet another aspect a method for positioning an osteochondral plug within a bone defect, the method includes the step of obtaining a surgical instrument that has an elongate shaft with proximal and distal ends, the distal end being configured to contact an osteochondral plug. The surgical instrument also includes a ribbon extending along the elongate shaft to form a loop at the distal end of the elongate shaft, the loop being sized to hold and secure the osteochondral plug to the distal end of the elongate shaft. Further, the surgical instrument includes a locking mechanism located near the proximal end of the elongated shaft for use in locking the ribbon relative to the elongate shaft and fixing the size of the loop, thereby securing the osteochondral plug to the distal end of the elongate shaft of the surgical instrument. The method also includes the steps of employing the surgical instrument to implant the osteochondral plug within the bone defect. The method provides for the implantation and then, removing the surgical instrument and ribbon from the bone defect site, leaving the osteochondral plug intact within the bone defect.

Yet another aspect of the present invention provides a method of fabricating a surgical instrument for facilitating the positioning of an osteochondral plug within a bone defect, the method includes the step of providing an elongate shaft with proximal and distal ends with a longitudinal axis extending therebetween. The distal end of the elongate shaft is configured to contact an osteochondral plug. The method also includes the step of providing a ribbon that extends along the elongate shaft and forms a loop at the distal end of the elongate shaft. The loop is sized and dimensioned to allow for the insertion and holding of the osteochondral plug. A further step of the method is providing an elongate sleeve that includes proximal and distal ends and a longitudinal axis extending therebetween. The elongate sleeve surrounds the elongate shaft facilitating holding the ribbon in place along the longitudinal axis of the elongate shaft. The method also includes the step of providing a locking mechanism positioned adjacent to the proximal end of the elongate shaft for selectively locking the ribbon relative to the elongate shaft.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

BEST MODE FOR CARRYING OUT THE INVENTION

Generally stated, disclosed herein is a surgical tool and a method for facilitating the positioning and implantation of (for example) an osteochondral bone plug into a bone defect located in the distal aspect of a femoral condyle. Further described herein is a method for attaching an osteochondral bone plug to a surgical tool without damaging the articular cartilage of the osteochondral plug graft. Also described herein is a method for positioning an osteochondral plug within a bone defect, and a method for fabricating a surgical instrument for use in positioning an osteochondral plug within a bone defect site.

Figure 1:
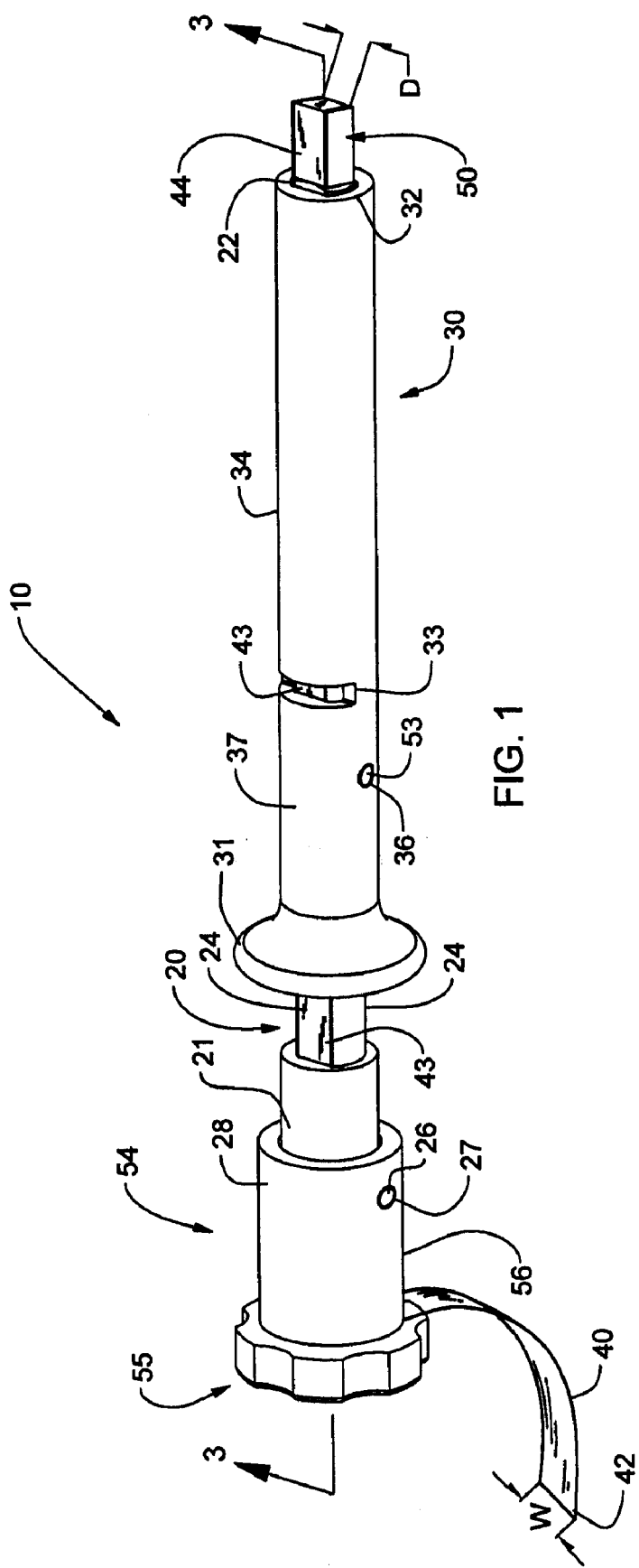
FIG. 1 is an isometric view of one embodiment of a surgical instrument, shown with a ribbon securing an osteochondral plug to a distal end of an elongate shaft, in accordance with an aspect of the present invention.
Figure 2:
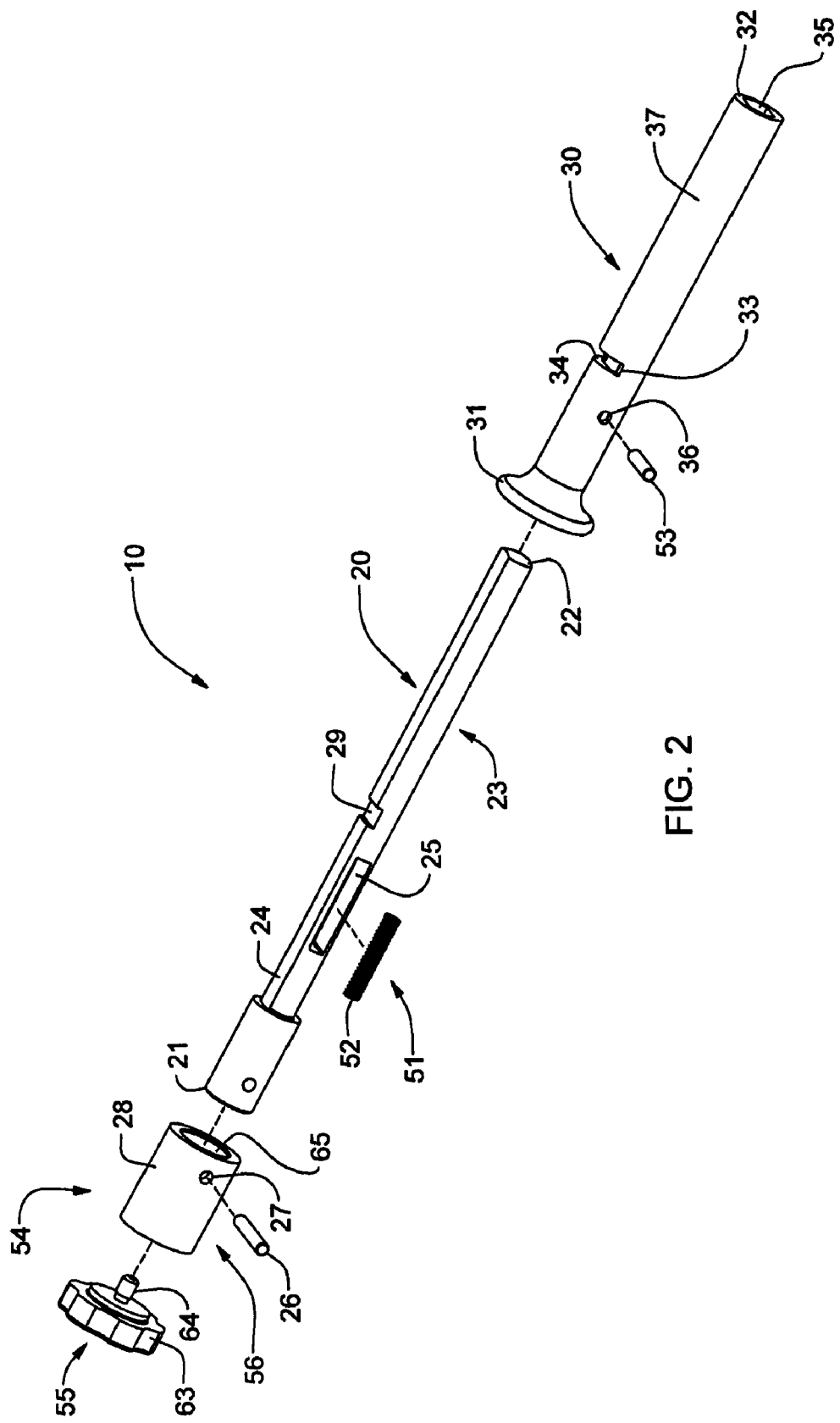
FIG. 2 is an isometric, exploded view of the surgical instrument of FIG. 1, in accordance with an aspect of the present invention.
Figure 3:
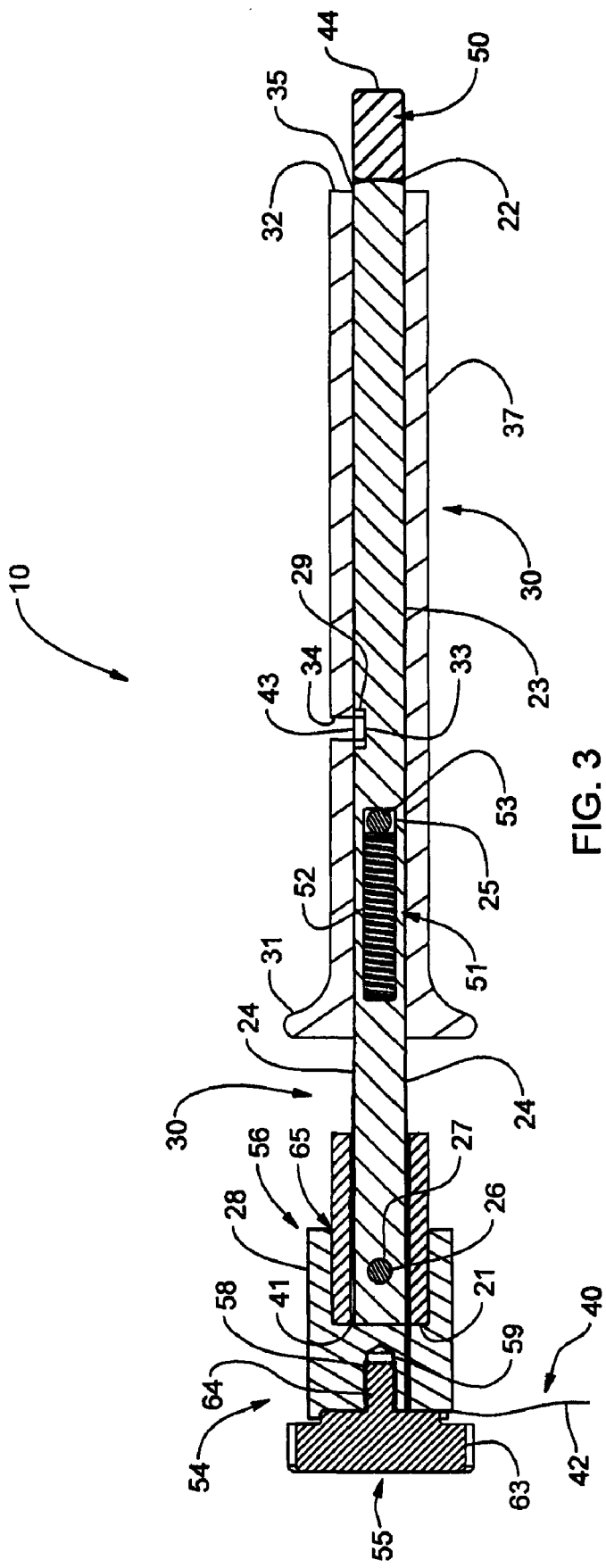
FIG. 3 is a cross-sectional, side elevational view of the surgical instrument of FIG. 1, taken along line 3-3, in accordance with an aspect of the present invention.

One embodiment of a surgical instrument 10, in accordance with an aspect of the present invention, is illustrated in FIGS. 1-3 and described below.

As shown in FIG. 1, surgical instrument 10 includes an elongate shaft 20 that has a proximal end 21 and a distal end 22 with a longitudinal axis extending therebetween. Distal end 22 of elongate shaft 20 is shaped to contact the articular cartilage portion of an osteochondral bone plug graft 50 without damaging the articular cartilage surface of the graft. The surface of distal end 22 is generally planar, though other configurations, including convex and concave surfaces, are contemplated herein to ensure intimate and non-damaging contact and securement of osteochondral plug 50. The shaft portion 23 of elongate shaft 20 has a generally oblong cross-section with opposing flat sides 24 extending typically the entire length of elongate shaft 20 including through the inner portion of proximal end 21 (see FIG. 3). The cross-section of elongate shaft 20 is sized to allow for insertion of the shaft into a center bore 35 of elongate sleeve 30. Positioned proximate to proximal end 21 is a rectangular shaped passage 25 that passes completely through the center of shaft portion 23. Passage 25 is appropriately sized and dimensioned to receive a press-fit spring 52 for use as part of a coupling mechanism 51. Proximal end 21 of elongate shaft 20 has a cylindrical outside configuration that is constructed with a diameter that is usually larger than the oblong cross-section of shaft portion 23. The cylindrical outer configuration of proximal end 21 slidingly engages a correspondingly generally cylindrical shaped clamp 56 that may then be attached to proximal end 21 utilizing a clamp pin 26.

As seen in FIG. 2, clamp pin 26 is constructed to a length that allows for it to be press-fit and secured within a transverse hole 27 having a length that extends diametrically through the one external wall 28 of clamp 56 and continuing through proximal end 21 exiting the opposing second external wall 28 of clamp 56. Also depicted in FIG. 2 is a notch 29 positioned on one of the flat sides 24 of shaft portion 23. Notch 29 may be oriented to align with a transverse slot 33 located within a sidewall 34 of the elongate sleeve 30. Notch 29 in combination with slot 33 allows the user of surgical instrument 10 to sever the ribbon 40 through slot 33 following final positioning and implantation of osteochondral bone plug graft 50.

Surgical tool 10 further includes an elongate sleeve 30 that has a proximal end 31, a distal end 32 and as described above, a transverse slot 33 positioned along a sidewall 34 and oriented about normal relative to the longitudinal axis extending between proximal end 31 and distal end 32. Elongate sleeve 30 is generally cylindrical in shape and includes center bore 35. Center bore 35 is sized and dimensioned to surround shaft portion 23, preferably functioning to protect and maintain alignment of ribbon 40 along flat sides 24 of the elongate shaft. Transverse slot 33 penetrates sidewall 34 and provides visualization of center bore 35 and ribbon 40. Further, the width of transverse slot 33 is large enough to accommodate standard surgical cutting tools, thereby allowing the user to cut any material that passes beneath slot 33.

As shown in FIGS. 1 and 2, the external surface 37 of proximal end 31 radially expands to allow for ease of use by the user when elongate sleeve 30 is moved from an extended position to a retracted position during the implantation of osteochondral plug 50. It should be understood to those skilled in the art that the shape and configuration of external surface 37 of proximal end 31 is for example purposes only and that other more ergonomically designed configurations may be considered for use in surgical instrument 10. As depicted in FIGS. 2 and 3, a sleeve pin 53 is constructed to a length that allows for it to be press-fit and secured within a second transverse hole 36. Transverse hole 36 has a length that extends diametrically through sidewall 34, exiting out the opposing sidewall 34 of elongate sleeve 30. During the assembly process, sleeve pin 53 is inserted through transverse hole 36 after elongate sleeve 30 has been slid into place over shaft portion 23. Following insertion, the ends of sleeve pin 53 are in contact with the two diametrically opposed sidewalls 34. The center section of sleeve pin 53 is positioned within passage 25 and interfaces with one end of spring 52. Coupling mechanism 51 of surgical instrument 10 preferably includes, in combination, the inserted sleeve pin 53 and spring 52. Upon mechanically coupling elongate sleeve 30 to elongate shaft 20 via coupling mechanism 51, elongate sleeve 30 is spring-biased relative to elongate shaft 20 and may be moved from an extended position to a retracted position.

Figure 4:
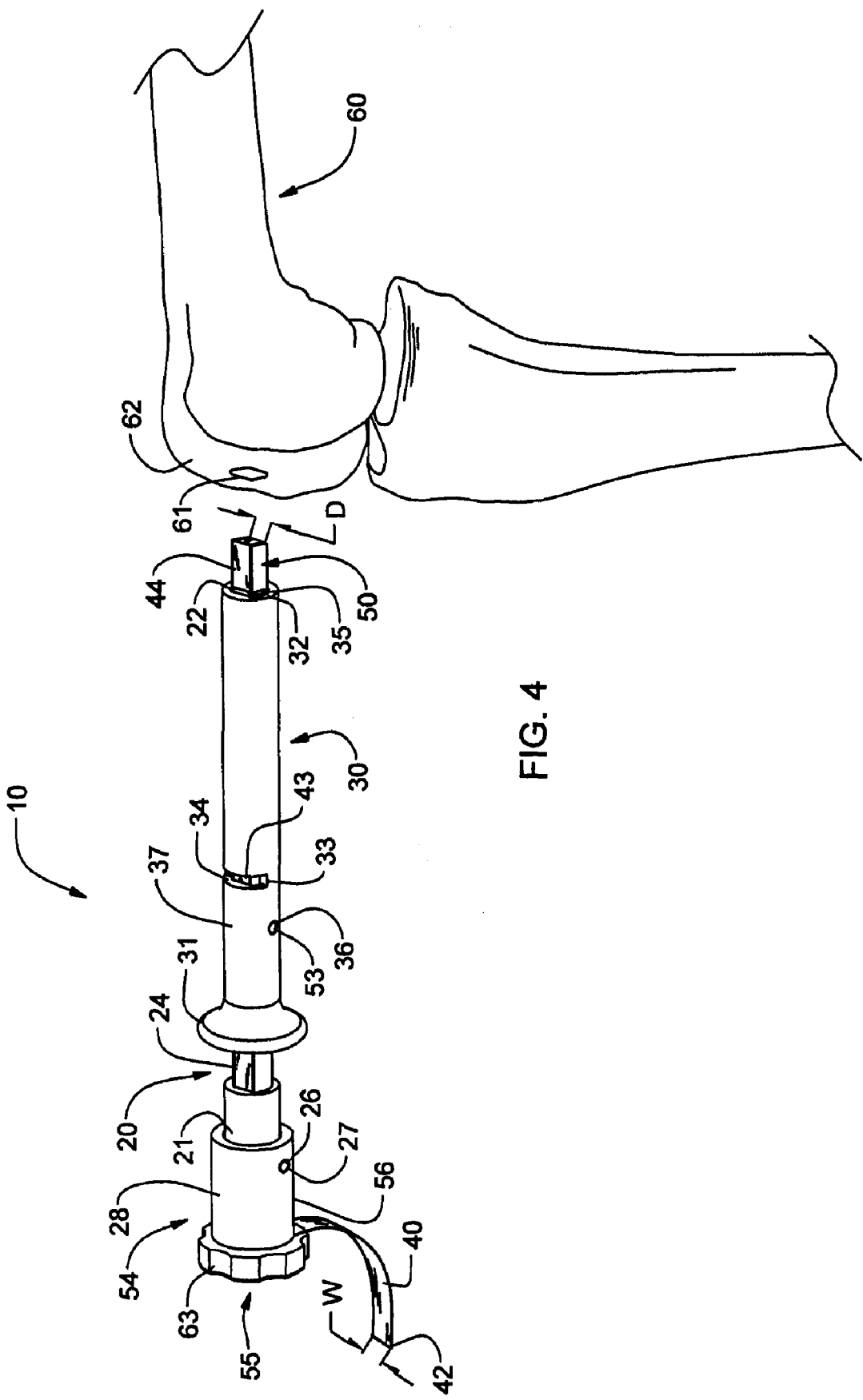
FIG. 4 is an isometric view of the surgical instrument of FIG. 1 positioned adjacent to a distal condyle of a human femur with an elongate sleeve in an extended position, and an osteochondral plug is attached to the distal end of an elongate shaft, shown prior to implanting the osteochondral plug within a bone defect, in accordance with an aspect of the present invention.
Figure 5:
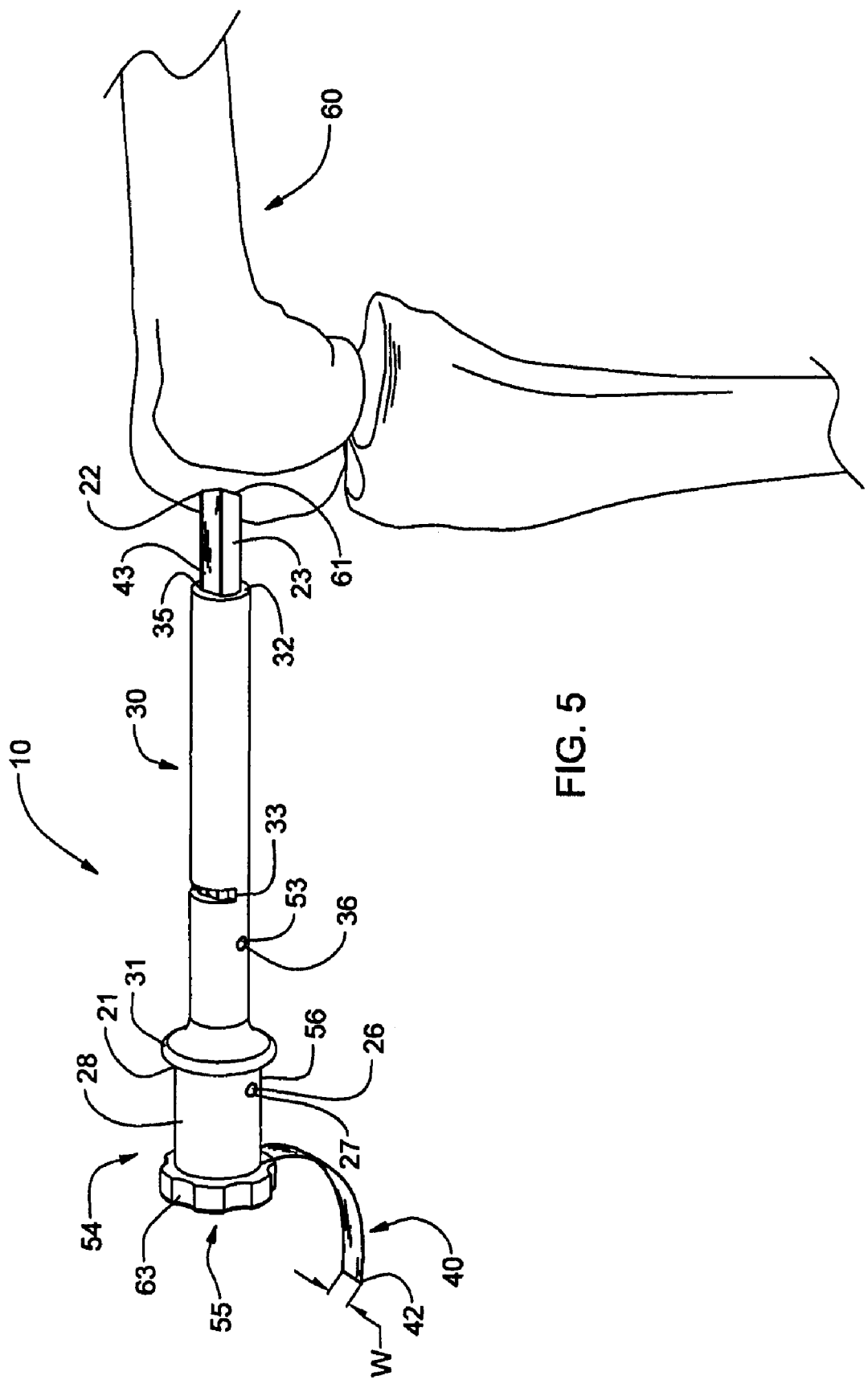
FIG. 5 is an isometric view of the surgical instrument of FIG. 4 positioned adjacent to the distal condyle, shown with the elongate sleeve in a retracted position, and the osteochondral plug (attached to the distal end of the elongate shaft) positioned within the condylar bone defect, in accordance with an aspect of the present invention.

As seen in FIG. 4, elongate sleeve 30 is oriented in the extended position with distal end 22 of elongate shaft 20 and distal end 32 of elongate sleeve 30 being substantially adjacent and parallel relative to each other. Elongate sleeve 30 is shown in FIG. 5 in the retracted position which allows the user of surgical instrument 10 to observe the position of osteochondral plug 50 when inserting the plug into a bone defect 61 before osteochondral plug 50 has been detached from surgical instrument 10. The user of surgical instrument 10 may move elongate sleeve 30 into the retracted position several times during the implantation procedure in order to ensure that proper placement of osteochondral plug 50 within bone defect 61 and the surrounding surface contour of the femur 60 has been achieved.

FIGS. 1 and 3 depict ribbon 40 positioned with surgical instrument 10, securing osteochondral plug 50 to distal end 22. Ribbon 40 includes a first end 41, a second end 42 with a narrow band-like structure 43 extending between the two ends. The overall length of ribbon 40 varies depending upon the application of use and the size of surgical instrument 10. Typically, ribbon 40 may come in a plurality of thicknesses dependent upon material quality, composition and use in situ. As shown in FIG. 1, ribbon 40 is fabricated from a substantially flexible and inert material. Materials that may be used for manufacturing of ribbon 40 include, but are not limited to UHMW polyethylene, thermoplastic polymers, thermosetting polymers, ferrous metals, non-ferrous metals, elemental metals, metal alloys, fiber reinforced materials, carbon based materials, Mylar®, Teflon®, PEEK, ABS polymers, polyethylene terephthalate, polyester film, polyester fiber, tetrafluoroethylene polymer, fluoro polymers, fluorocarbon resins, TFE copolymers, polytetrafluroethylene and polyamides. Also, the ribbon can be made out of a natural fiber or combination of fibers such as nylon, Dacron®, Gore-Tex® and cotton.

Further, ribbon 40 may be constructed of a biologic material such as Type I collagen, Type II collagen, Type IV collagen, fibrin, hyaluronan, alginate, chitosan, gelatin, agarose, cell-contracted collagen containing proteoglycans, glycosaminoglycans or glycoproteins, polymers of aromatic organic acids, fibronectin, laminin, bioactive peptide growth factors, cytokines, elastin, fibrin, synthetic polymeric fibers made of poly-acids such as polylactic, polyglycolic or polyamino acids, polycaprolactone, absorbable epsilon caprolactone polymer, polypeptide gel, copolymers thereof and combinations thereof. As stated above, ribbon 40 is biocompatible, biodegradable, flexible hydrophilic, non-reactive, has a neutral charge and is able to have or has a defined shape and structure.

As shown in FIGS. 1, 4, 5 and 6, ribbon 40 is generally sized with a width W that is equal or smaller than the width D of osteochondral plug 50. The basis for this size relationship is because width W of ribbon 40 must be equal to or less than width D of osteochondral plug 50 to allow for accurate and intimate placement of osteochondral plug 50 within bone defect 61. In the event width W is greater than width D, the close fit necessary for the bone graft to integrate with the host defect site will likely not occur because of possible interference of the edges of ribbon 40 with the side walls of bone defect 61 and the sides of osteochondral plug 50. Further, the width size relationship is important to facilitating removal of ribbon 40 following final placement of osteochondral plug 50 within bone defect 61. Osteochondral plug 50 is typically square or rectangular shaped, though it should be understood to those skilled in the art that other shapes are contemplated and may be utilized when forming the outside configuration of osteochondral plug 50, including, but not limited to oval, oblong, circular or derivations of these non-polygonal shapes, as well as triangular, hexagonal and other polygonal shapes.

As shown in FIGS. 1 and 3, when ribbon 40 is secured within surgical instrument 10 extending along flat sides 24, band 43 forms a loop 44 at distal end 22 of elongate shaft 20. The size of loop 44 is dependent upon the size of osteochondral plug 50 and the amount of tension that a user places on ribbon 40 following insertion of osteochondral plug 50 within loop 44. Prior to use in positioning osteochondral plug 50 within bone defect 61, first end 41 is fixed in place at proximal end 21 of elongate shaft 20 by the clamp 56. Ribbon 40 is located along one flat side 24 of elongate shaft 20, around distal end 22 and then up the opposing flat side 24. Second end 42 is passed through an internal slot 59 positioned within clamp 56, exiting out of proximal end 21. Loop 44 is formed by placing tension on band 43 at distal end 22, thereby urging band 43 to slide in a distal direction resulting in an increase in loop 44 size. Loop 44 size is fixed by engaging locking mechanism 54 in a locked position and securing the position of second end 42 and the length of band 43. Preferably, fixing the size of loop 44 usually occurs after osteochondral plug 50 is placed between loop 44 and distal end 22 with second end 42 being pulled to tighten loop 44 around osteochondral plug 50 and firmly hold osteochondral plug 50 against distal end 22. Following the tightening of ribbon 40, locking mechanism 54 is actuated from an unlocked position to a locked position.

FIG. 2 depicts locking mechanism 54 disposed at proximal end 21. Locking mechanism 54 typically includes a bolt 55 and clamp 56. Bolt 55 (i.e., one example of the locking member), may comprise a handle portion 63 with a threaded post 64 extending from the undersurface of handle portion 63. Clamp 56 is (in one embodiment) a unitary cylindrical body with a non-through central lumen 65 at one end of clamp 56 and a centralized generally smaller threaded hole 58 located at the opposite end. As described above, clamp 56 and elongate shaft 20 are connected following the insertion of proximal end 21 into a central lumen 65. Clamp pin 26 is then inserted into transverse hole 27 securing clamp 56 to proximal end 21. As seen in FIG. 3, clamp 56 further includes internal slot 59 through which second end 42 passes before exiting through the proximal end of clamp 56. Locking mechanism 54 is in an unlocked position when threaded post 64 of bolt 55 is loosely threaded into threaded hole 58. When locking mechanism 54 is in the locked position, threaded post 64 fully engages threaded hole 58 until the undersurface of handle portion 63 abuts the proximal surface of bolt 55 securing second end 42 of ribbon 40 therebetween. First end 41 remains generally fixed by clamp 56 when locking mechanism 54 is in both locked and unlocked positions.

The method for securing an osteochondral plug graft to a surgical instrument includes obtaining a surgical instrument 10 which includes elongate shaft 20 with distal end 22 shaped and configured to contact osteochondral plug 50. Surgical instrument 10 also includes ribbon 40 that extends along opposing flat sides 24 of elongate shaft 20. Ribbon 40 forms loop 44 to accommodate osteochondral plug 50 at distal end 22. Further included in the construct of surgical instrument 10 is locking mechanism 54 that is typically disposed at proximal end 21 of elongate shaft 20. Locking mechanism 54 secures ribbon 40 in place relative to elongate shaft 20 to maintain the appropriate sized loop 44 at distal end 22 when in a locked position (as described above). The method further includes placing osteochondral plug 50 within loop 44 and applying tension via second end 42 to adjust the overall length of ribbon 40, thereby causing loop 44 to tighten around osteochondral plug 50 and secure osteochondral plug 50 to distal end 22. It should be understood that the method may include engaging locking mechanism 54 to a locked position (as described above) in order to fix ribbon 40 and loop 44 size relative to elongate shaft 20 resulting in the securement of osteochondral plug 50 to distal end 22.

The method for positioning an osteochondral plug graft within a femoral distal condyle bone defect includes obtaining a surgical instrument 10 including elongate shaft 20 with distal end 22 shaped and configured to contact osteochondral plug 50. Surgical instrument 10 typically has ribbon 40 that extends along opposing flat sides 24 of elongate shaft 20 forming a loop 44 at distal end 22 that is sized to receive osteochondral plug 50. Surgical instrument 10 includes locking mechanism 54 that is typically disposed at proximal end 21 of elongate shaft 20. Locking mechanism 54 when actuated to a locked position locks ribbon 40 relative to elongate shaft 20 to maintain the appropriately sized loop 44 at distal end 22, resulting in the securement of osteochondral plug 50 to distal end 22.

As shown in FIG. 4, the method further includes positioning osteochondral plug 50, while secured to surgical instrument 10, into bone defect 61 located in a distal condyle of femur 60. As shown in FIG. 5, elongate sleeve 30 may be moved to a retracted position, allowing the user to see the position and orientation of bone plug 50 within bone defect 61. In the event osteochondral plug 50 is not placed in a satisfactory position, the user may withdraw osteochondral plug 50 from the host defect site and reorient osteochondral plug 50 and attempt to implant osteochondral plug 50 again. The securement mechanism utilized with surgical instrument 10 allows the user to reposition the plug graft numerous times without damaging either the host bone site or osteochondral plug 50.

Figure 6:
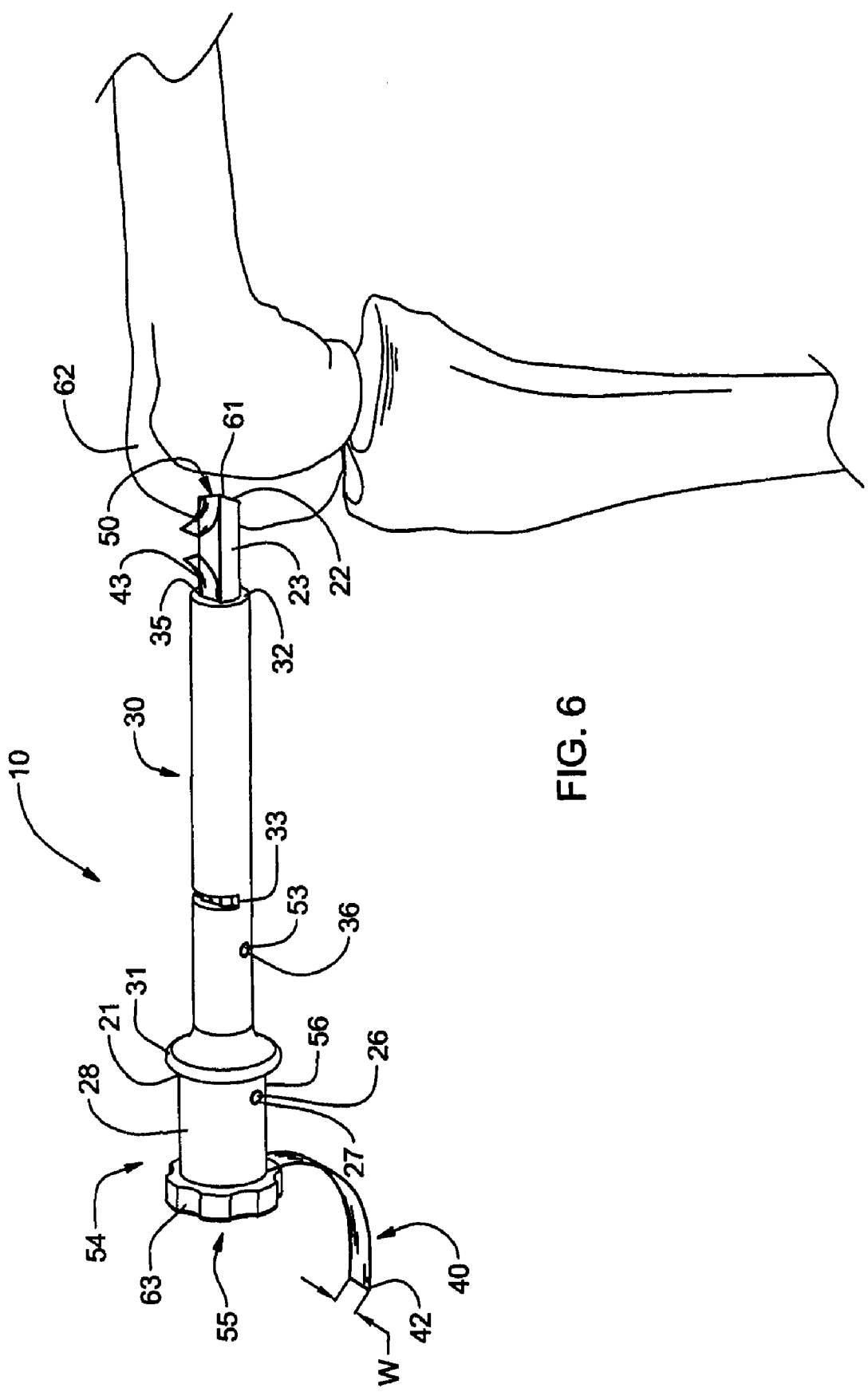
FIG. 6 is an isometric view of the surgical instrument of FIGS. 4 & 5 positioned adjacent to the distal condyle, shown with the elongate sleeve in the retracted position following cutting and partial withdrawal of the ribbon from the bone defect site, with the osteochondral plug remaining intact within the bone defect, in accordance with an aspect of the present invention.

As depicted in FIG. 6, following final placement of osteochondral plug 50 by the user, band 43 of ribbon 40 is severed through slot 33 in elongate sleeve 30. The user loosens bolt 55 to release end 42 allowing ribbon 40 to be pulled proximally along flat side 24 and exiting from surgical instrument 10 at the proximal end of clamp 56. Following ribbon's 40 withdrawal from beneath implanted osteochondral plug 50 and out of bone defect 61, osteochondral plug 50 is left implanted within the host site and surgical instrument 10 is then typically moved away from femur 60.

A method for fabricating a surgical instrument that is to be used for positioning a plug graft within a bone defect site includes providing elongate shaft 20 that includes proximal end 21 and distal end 22, wherein distal end 22 is designed to contact and protect osteochondral plug 50. Further, surgical instrument 10 is fabricated by providing, typically, ribbon 40 that extends along opposing flat sides 24 of shaft portion 23 to form loop 44 at distal end 22. Loop 44 is generally sized to capture osteochondral plug 50. Additionally, surgical instrument 10 is fabricated by providing elongate sleeve 30 that has proximal and distal ends 31, 32. When assembled, elongate shaft 20 is slid into center bore 35 of elongate sleeve 30 resulting in elongate sleeve 30 surrounding shaft portion 23 and ribbon 40. Elongate sleeve 30 preferably functions to maintain position of ribbon 40 along flat sides 24 of shaft portion 23 as well as acting to protect ribbon 40. Surgical instrument 10 is also fabricated by providing locking mechanism 54 located at proximal end 21 of elongate shaft 20. Locking mechanism 54 is configured to actuate between a locked position and an unlocked position. When in the locked position, locking mechanism 54 locks ribbon 40 in a fixed position relative to elongate shaft 20 by securing second end 42. Locking mechanism 54 includes (in one embodiment) bolt 55 and clamp 56, with bolt 55 threadingly engaging threaded hole 58 disposed in proximal end of clamp 56.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A method of grasping an osteochondral plug, the method comprising: employing a surgical instrument comprising an elongate shaft with proximal and distal ends, and a longitudinal axis extending therebetween, the distal end of the elongate shaft being configured to contact an osteochondral plug; a ribbon extending along opposing sides of the elongate shaft and forming a loop at the distal end of the elongate shaft, wherein when in use, the loop is sized to receive the osteochondral plug to the distal end of the elongate shaft; an elongate sleeve having a proximal and a distal end, and a longitudinal axis extending therebetween, wherein the elongate sleeve surrounds the elongate shaft and facilitates holding the ribbon in place relative to the elongate shaft; and a locking mechanism disposed near the proximal end of the elongate shaft for locking the ribbon relative to the elongate shaft when in a locked position, wherein the locking mechanism includes a clamp and a rotatable bolt mounted to the clamp, the rotatable bolt being longitudinally movable between a proximal unlocked position wherein the ribbon is not locked and a distal locked position wherein the bolt engages and secures an end portion of the ribbon between a surface of the bolt and a proximal surface of the clamp, wherein the ribbon includes a first end portion secured by the clamp when the bolt is in the proximal unlocked position and in and opposite thereto, a second end portion which is releasably secured by the bolt; placing the osteochondral plug within the loop of the ribbon; pulling one end of the ribbon to adjust a length of the ribbon and thereby size of the loop to tighten the loop around the osteochondral plug; and engaging the locking mechanism to secure the ribbon relative to the elongate shaft and thereby secure the osteochondral plug to the distal end of the elongate shaft.

2. The method of claim 1, further comprising providing the osteochondral plug with a width D, and wherein the ribbon comprises a width W, wherein width W is equal to or less than width D.

3. The method of claim 1, wherein the employing further comprises providing the locking mechanism, the locking mechanism comprising a locking member threadably coupled to the proximal end of the elongated shaft for securing the ribbon relative to the elongate shaft when in a locked position, and wherein when in an unlocked position, the locking mechanism allows for removal of the ribbon from the elongate shaft.

4. The method of claim 1, wherein the employing further comprises providing the elongate shaft with at least one of a planar surface, a convex surface and a concave surface.

5. The method of claim 1, wherein the ribbon comprising a substantially flexible, biocompatible material.

6. The method of claim 1, wherein the ribbon is fabricated from at least one of UHMW polyethylene, thermoplastic polymer, thermosetting polymer, ferrous metal, non-ferrous metal, elemental metal, metal alloy, fiber reinforced material, carbon based material, PEEK, ABS polymers, nylon, polyethylene terephthalate, polyester film, polyester fiber, tetrafluroethylene polymer, fluoro polymers, fluorocarbon resins, TFE copolymers, polytetrafluroethylene and polyamides.

* * * * *

UNITED STATES PATENT AND TRADEMARK OFFICE
CERTIFICATE OF CORRECTION

| | | |
|---|---|---|
| PATENT NO. | : 7,887,546 B2 | Page 1 of 1 |
| APPLICATION NO. | : 12/794395 | |
| DATED | : February 15, 2011 | |
| INVENTOR(S) | : Gil et al. | |

It is certified that error appears in the above-identified patent and that said Letters Patent is hereby corrected as shown below:

On the Title Page, in Field (75), under "Inventors", in Column 1, Line 1, delete "Carols" and insert -- Carlos --, therefor.

In Column 3, Line 43, delete "proximal," and insert -- proximal --, therefor.

Signed and Sealed this
Fifth Day of April, 2011

David J. Kappos
*Director of the United States Patent and Trademark Office*